United States Patent [19]
Bowman

[11] Patent Number: 5,265,624
[45] Date of Patent: * Nov. 30, 1993

[54] STIMULATION COLLAR

[75] Inventor: Bruce R. Bowman, Eden Prairie, Minn.

[73] Assignee: EdenTec, Eden Prairie, Minn.

[*] Notice: The portion of the term of this patent subsequent to Jun. 23, 2009 has been disclaimed.

[21] Appl. No.: 885,470

[22] Filed: May 19, 1992

Related U.S. Application Data

[63] Continuation-in-part of Ser. No. 578,150, Sep. 6, 1990, Pat. No. 5,123,425.

[51] Int. Cl.⁵ ............ A61F 5/56; A61B 5/08; A61B 5/04
[52] U.S. Cl. ............ 128/848; 128/724; 128/733
[58] Field of Search ............ 128/848, 849, 859, 860, 128/724, 733, 774, 777; 340/573, 575, 626, 665, 668; 602/902

[56] References Cited

U.S. PATENT DOCUMENTS

| | | | |
|---|---|---|---|
| 2,999,232 | 9/1961 | Wilson | 340/279 |
| 3,480,010 | 11/1969 | Crossley | 128/848 |
| 3,998,209 | 12/1976 | Macvaugh | 340/279 |
| 4,220,142 | 9/1980 | Rosen | 340/525 |
| 4,440,160 | 4/1984 | Fischell | 340/407 |
| 4,669,477 | 6/1987 | Ober | 128/777 |
| 4,715,367 | 12/1987 | Crossley | 128/848 |
| 5,123,425 | 6/1992 | Shannon | 128/848 |

Primary Examiner—Michael A. Brown
Attorney, Agent, or Firm—John L. Rooney

[57] ABSTRACT

A system for the treatment of obstructive sleep apnea packaged in a collar assembly with remote electrodes which can be worn by a patient without any special preparation. The collar assembly has an adjustable attachment means, such as hook and latch, to accommodate variations in neck size. The collar assembly is properly oriented using variations in physical shape and/or color. An optional feedback system permits the patient to readily verify proper orientation. The remote electrodes may be conveniently maintained in position using a mouthpiece or other means. Radio frequency signals are sent from the collar assembly to the remote electrodes to provide the therapy upon detection of an apnea event.

14 Claims, 10 Drawing Sheets

STIMULATION COLLAR

CROSS REFERENCE TO CO-PENDING APPLICATIONS

The present application is a continuation-in-part of commonly assigned co-pending U.S. patent application Ser. No. 07/578,150 filed Sep. 6, 1990 and entitled Obstructive Sleep Apnea Collar, now U.S. Pat. No. 5,123,425.

BACKGROUND OF THE INVENTION

1. Field of the Invention—The present invention generally relates to medical devices, and more particularly, relates to treatment using electrical stimulation.

2. Description of the Prior Art—Sleep apnea is a medical condition which effects a large segment of the population. It exists in several forms. Perhaps the most dangerous, called central apnea, is associated with a lack of central drive to breath or with a disruption of the neural pathways from the brain to the diaphragm muscles. Research has been progressing for some time with one mode of treatment being electrical stimulation of the phrenic nerve, thereby controlling function of the diaphragm. William W. L. Glenn describes the nature of this research in "Diaphragm Pacing: Present Status" in Pace, Volume 1, pages 357-370, July-September 1978.

A second form of sleep apnea, and of most concern to the present invention, is that which obstructs the upper air passageways. This condition has numerous deleterious results including disturbance of the patient and sleep partner and loss of effectiveness of the sleep process resulting in excessive patient fatigue, as well as long term effects including hypertension and cardiac problems.

The simplest forms of treatment for upper airway obstructive sleep apnea involve mechanical constraints. U.S. Pat. No. 4,304,227 issued to Samelson describes such a device. Various surgical techniques are also employed including tracheostomy.

Perhaps the most common technique is through the use of systems which detect the obstructive condition and alert the patient to the problem in some fashion. Examples of this type of system include: U.S. Pat. No. 2,999,232 issued to Wilson; U.S. Pat. No. 3,032,029 issued to Cunningham; U.S. Pat. Nos. 3,480,010 and 4,715,367 issued to Crossley; U.S. Pat. No. 3,593,703 issued to Gunn et al.; U.S. Pat. No. 3,696,377 issued to Wall; U.S. Pat. No. 3,998,209 issued to Macvaugh; U.S. Pat. No. 4,220,142 issued to Rosen et al.; and U.S. Pat. No. 4,593,686 issued to Lloyd et al. These devices employ a variety of techniques, but each tends to be based upon detection of the condition and production of an alarm. Unfortunately, the alarm may rouse the patient to the extent that the patient's sleep is disturbed, thereby exacerbating the very problems caused by the apnea episode.

Recently, research has been conducted which shows that the obstruction within the upper air passageway may be cleared with electrical stimulation. Two articles, herein incorporated by reference, describing this research may be found in American Review of Respiratory Disease Volume 140, 1989 at pages 1279 through 1289. The first article is "Effects of Electrical Stimulation of the Genioglossus on Upper Airway Resistance in Anesthetized Dogs", by Hiroshi Miki et al. The second article is "Effects of Submental Electrical Stimulation during Sleep on Upper Airway Patency in Patients with Obstructive Sleep Apnea", also by Hiroshi Miki et al.

U.S. Pat. No. 4,830,008 issued to Meer discusses an implantable system for treatment of obstructive sleep apnea using electrical stimulation. U.S. Pat. No. 4,669,477 issued to Ober shows a similar system for the treatment of bruxism.

SUMMARY OF THE INVENTION

The present invention overcomes the disadvantages found in the prior art systems by providing an external device for the effective treatment of obstructive sleep apnea using a collar which may be easily and properly attached by the patient. The collar senses the onset of an apnea episode. Automatically, the circuitry within the collar begins the stimulation therapy. Because the collar is worn externally, it is easily and inexpensively attached and removed.

The stimulation may be applied from electrodes located within the collar. However, for stimulation sites not directly accessible by the collar electrodes, available remote electrodes may be employed. The electronic circuitry within the collar is coupled to the remote electrodes by a radio frequency link. To be most effective, antennae located within the collar must be placed with a particular orientation with respect to the remote electrodes to minimize the transmission distance, and maximize antenna coupling. In one preferred embodiment, the remote electrodes are fixedly attached to a mouthpiece. The location of the remote electrodes on the mouthpiece ensure optimal orientation with respect to a properly installed collar when the mouthpiece is seated over the teeth of the patient.

The collar is readily attachable using hook and latch or other suitable fasteners. Means located on the collar ensure proper placement of the sensor and antennae with respect to the patient. The positioning means can take the form of variations in shape or color of the collar. The collar is attractive and comfortable, and therefore, promotes patient compliance through ease of use. The mouthpiece or other means of mounting the remote electrodes are similarly easy to use and comfortable. The collar, remote electrodes, or both may be made in disposable form to ensure ease of manufacture.

A sensor located on or near the collar is used to determine the onset of an apnea episode. Proper functioning of the respiratory system may be monitored directly in the form of air flow, direct or indirect blood gas measurements (such as pulse oxygen saturation), or indirectly via breath or snoring sounds, breath temperature, pressure sensors, thoracic impedance, strain gauges, or airway resistance. The output of the sensor is conditioned and interpreted, and used to determine whenever an apnea event is in process. An automatic cycling mode provides prophylactic therapy without the need for a sensor input.

After an apnea event has been detected, a radio frequency signal is transmitted from antennae within the collar to remote electrodes providing both power and control information. The remote electrodes are optimally placed for stimulation of the targeted muscles such as the genioglossus and related muscle groups of the upper air passageway. The remote electrodes may be held in a fixed position by attachment to a mouthpiece. The upper airway opens as a result of the stimulation signals applied by the remote electrodes.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
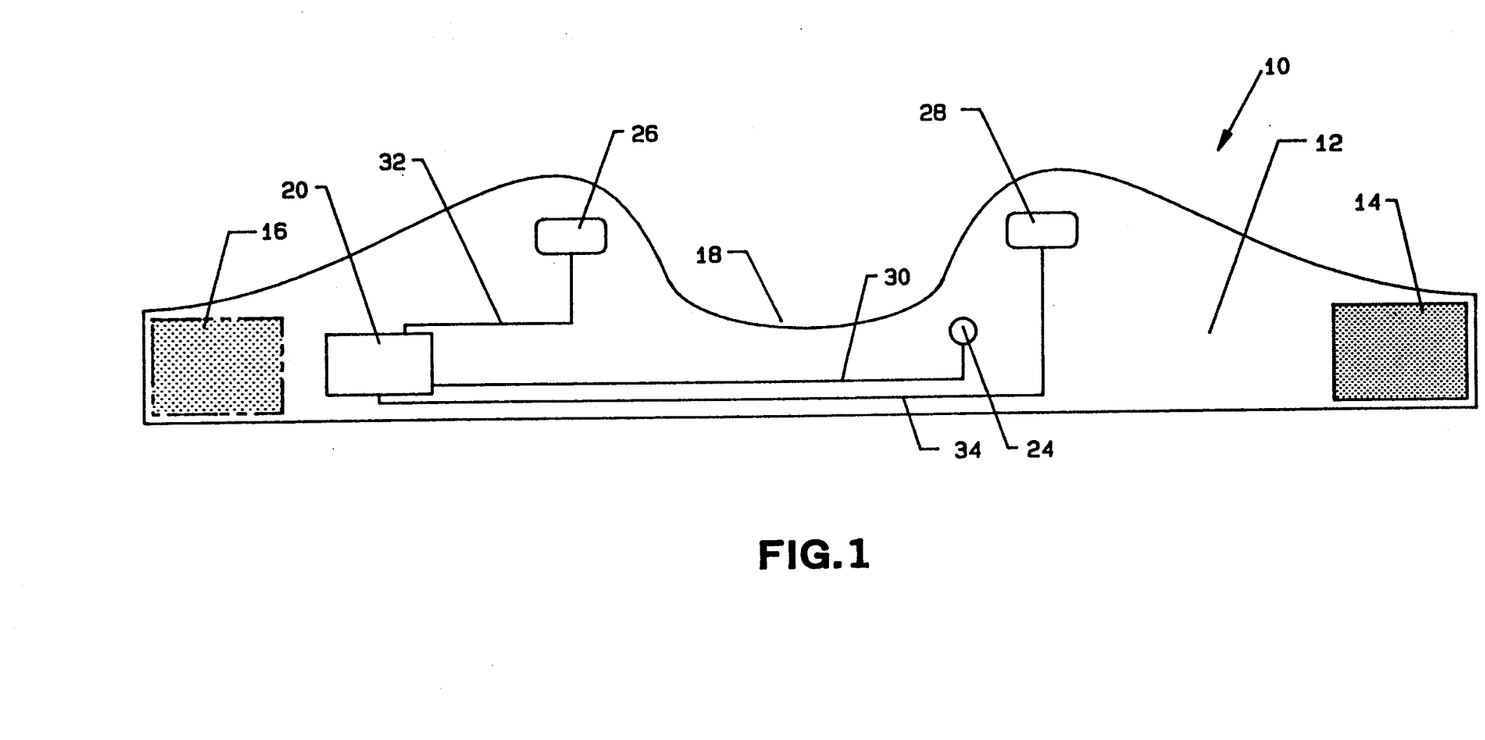
FIG. 1 is a plan view of the collar assembly.

FIG. 1 is a plan view of collar assembly 10 of the present invention. The main substrate 12 is of a flexible material suitable for wrapping about the patient's neck. Preferably, main substrate 12 is of a porous woven material which permits the collar to "breathe". Main substrate 12 is fastened about the neck of the patient using convenient fasteners such as hook 14 and latch 16 (see also FIGS. 4 and 5). Preferably, hook 14 and latch 16 are sufficiently wide to permit adjustment to necks of varying sizes.

It is important that collar assembly 10 be properly positioned when attached to the neck of the patient to ensure that the components located on main substrate 12 (e.g. sensors and antennae) are properly positioned. In the preferred embodiment, this is accomplished with chin notch 18 which accommodates the chin of the patient. In this way, the patient can easily feel that collar assembly 10 is properly positioned.

Sensor 24 is used to determine the onset of an apnea episode. In the preferred embodiment, this is a microphone or motion sensor which generates an electrical signal corresponding to the presence of breath or snoring sounds. Other sensors which may be used include an oximeter to measure the percentage of oxygen saturation of the blood, an airflow sensor, an airway resistance sensor, a strain gauge, or an impedance plethysmograph. Sensor 24 is fixedly mounted to main substrate 12 such that when collar assembly 10 is positioned using chin notch 18, sensor 24 is properly located for its monitoring function. Depending on the sensor used, sensor 24 may be mounted elsewhere, such as under the nose (i.e. air flow) or on a finger or ear (i.e. pulse oximetry). Sensor 24 is electrically coupled to electronic module 20 using cable 30. Electronic module 20 contains the circuitry to process the sensor output and generate radio frequency signals as required. Electronic module 20 is discussed in more detail below.

The radio frequency signals generated by electronic module 20 are coupled to antenna 26 and antenna 28 via cable 32 and cable 34, respectively. Antennae 26 and 28 are selected based upon the radio frequencies to be transmitted in accordance with the choice of remote electrodes and according to orientation of the remote electrodes. For instance in an alternative embodiment, antennae 26 and 28 could be replaced with a single circumferential antenna that communicates independently and powers both remote electrodes. The antennae are fixed to main substrate 12 such that they will be properly located to most effectively transmit the radio frequency signals to the remote electrodes. As explained in more detail below, the remote electrodes are located to efficiently stimulate the targeted muscles, such as the genioglossus and related muscle groups of the upper air passageway.

Figure 2:
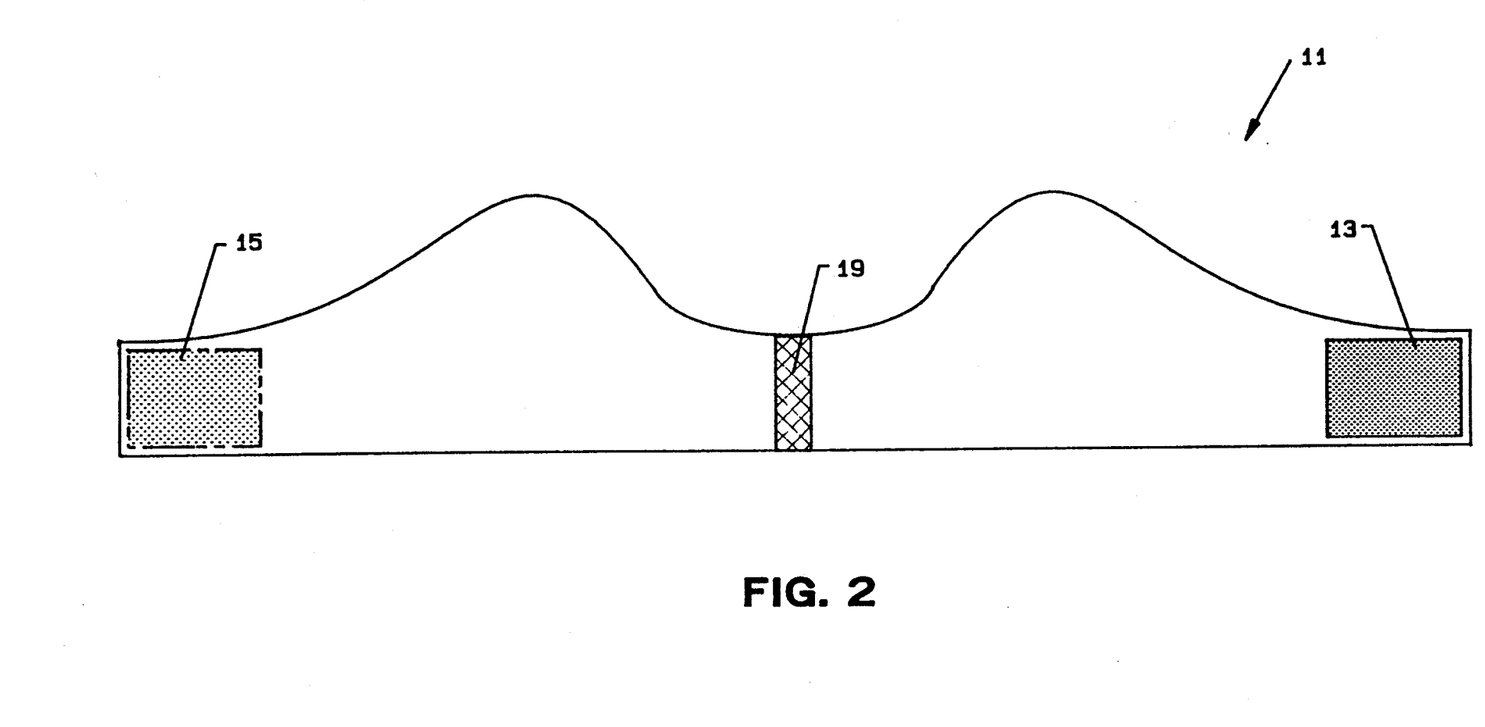
FIG. 2 is a collar assembly showing an alternative positioning means.

FIG. 2 shows collar assembly 11 employing a first alternative positioning means. Collar assembly 11 has a color stripe 19 which the patient positions over his epiglottis. Collar assembly 11 is constructed such that color stripe 19 is located the proper distance from hook 13 and latch 15.

Figure 3:
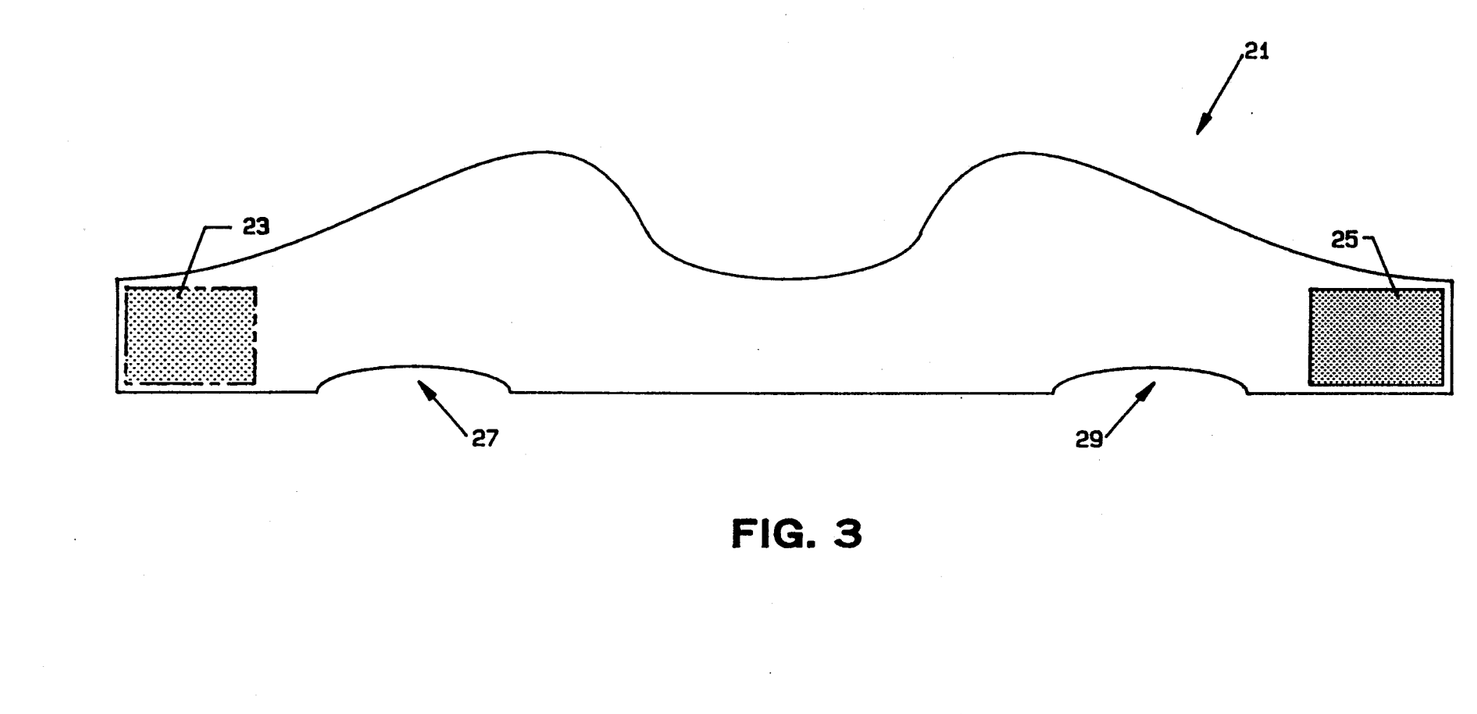
FIG. 3 is a collar assembly showing a second alternative positioning means.

FIG. 3 is a plan view of collar assembly 21 using a second alternative positioning means. Collar assembly 21 employs shoulder notches 27 and 29 which are spaced appropriately from hook 23 and latch 25. Unlike chin notch 18 (see also FIG. 1), shoulder notches 27 and 29 are located along the bottom surface of collar assembly 21.

Figure 4:
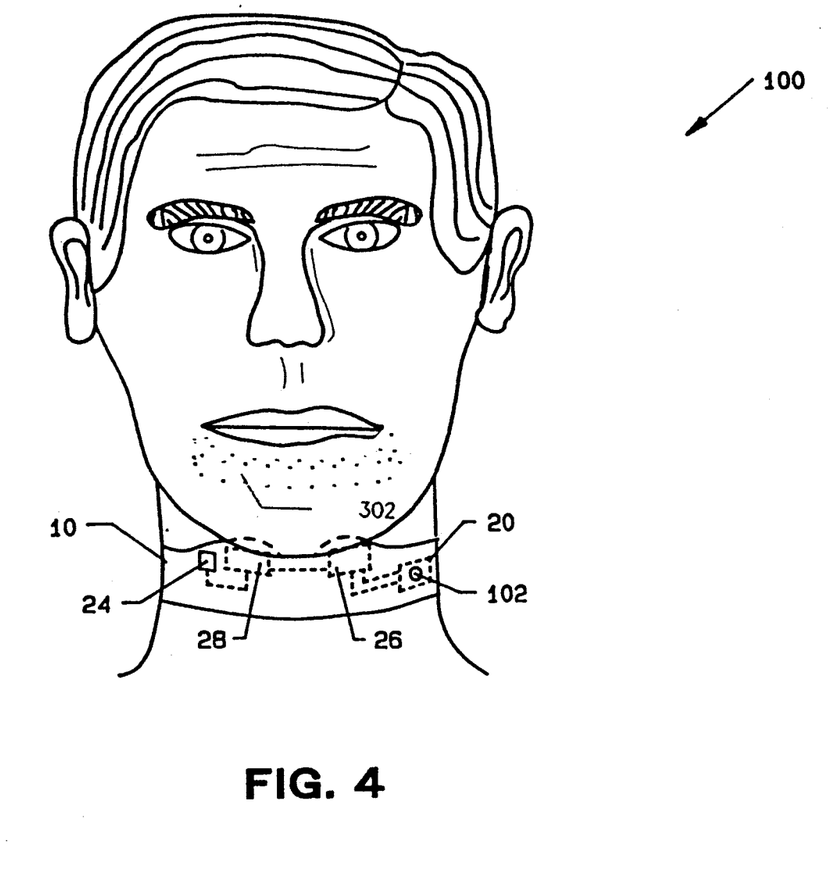
FIG. 4 is a frontal view of a patient having properly positioned collar assembly and mouthpiece of the present invention.

FIG. 4 is a frontal view of patient 100 with collar assembly 10 properly positioned for treatment. The location of mouthpiece 302 is shown in phantom to illustrate the proximity between antennae 26 and 28 and the remote electrodes (not shown in this view) of mouthpiece 302. All other referenced elements are as previously discussed.

Figure 5:
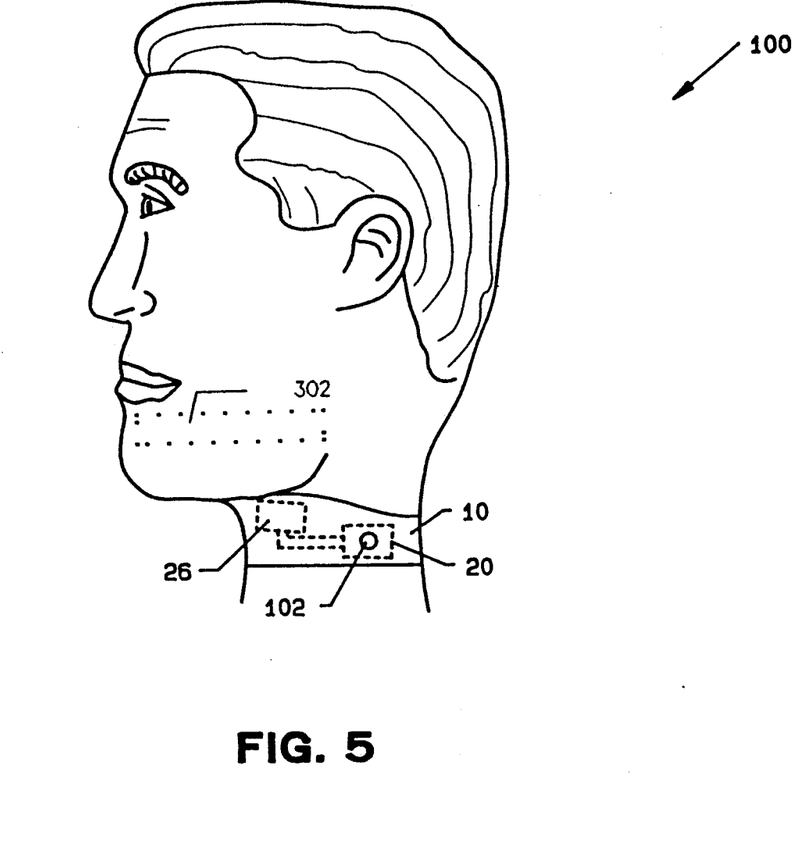
FIG. 5 is a side view of the patient of FIG. 4.

FIG. 5 is a side view of patient 100 with collar assembly 10 and mouthpiece 302 (in phantom) in position. Also shown is optional feedback positioning push button 102. The use of push button 102 provides patient 100 with positive verification that collar assembly 10 and mouthpiece 302 have been properly positioned. Push button 102 is depressed by patient 100 to manually activate the radio frequency signal from collar assembly 10, thereby causing the remote electrodes (not shown in this view) to stimulate the muscle groups of the upper air passageway. If collar assembly 10 and mouthpiece 302 are properly positioned, patient 100 will notice a slight contraction of the appropriate musculature.

Figure 6:
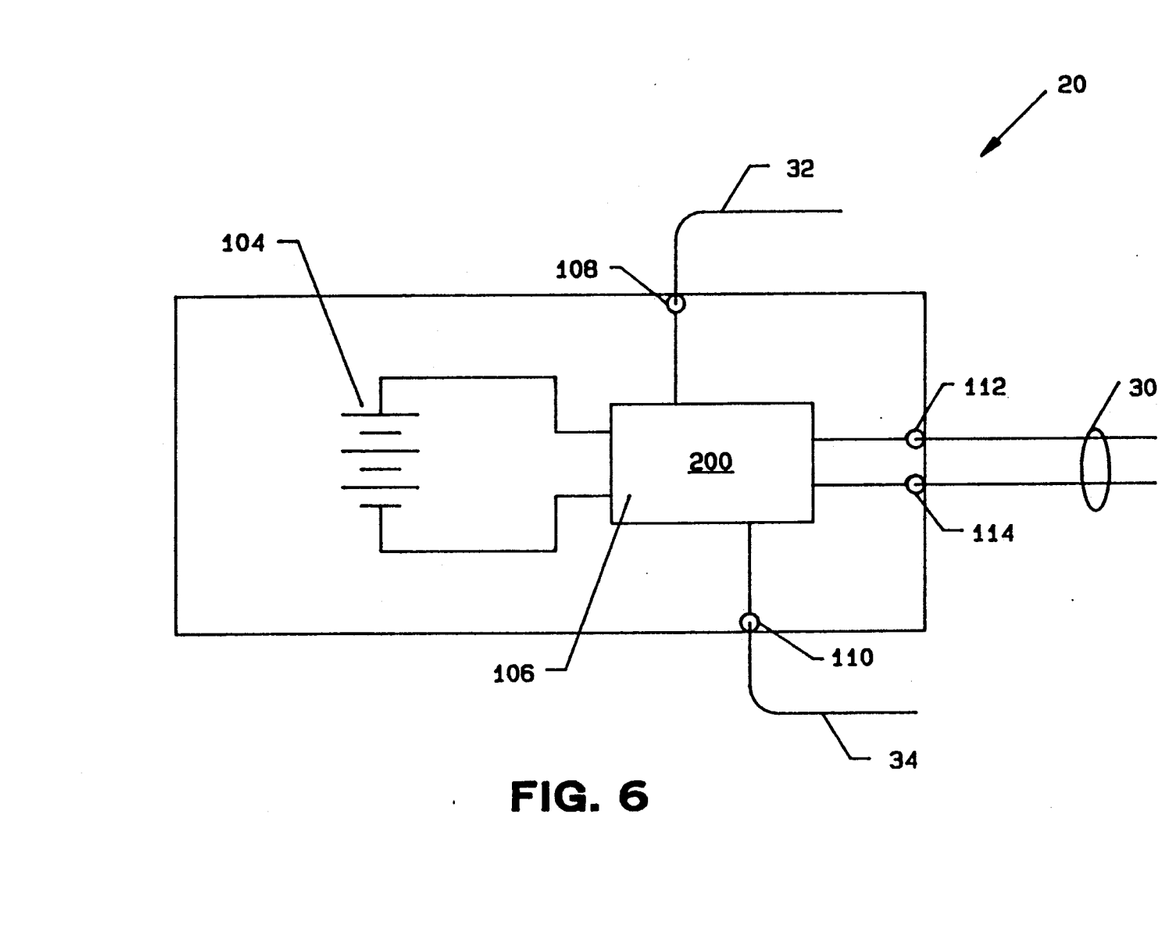
FIG. 6 is an overall view of the electronic module of the collar assembly.

FIG. 6 is a schematic view of electronic module 20 showing its major components. Electronic circuit 200 is powered by primary battery 104 which may or may not be mounted on collar assembly 10. Electronic circuit 200 is preferably a custom integrated circuit, but more probably is a hybrid.

Electronic circuit 200 may or may not be mounted on collar assembly 10 and has one input cable 30 from sensor 24 and two output cables 32 and 34 coupled to antennae 26 and 28, respectively (see also FIG. 1). Because cables 32 and 34 must handle radio frequency signals, care must be exercised with construction and layout to provide efficient, reflection free transmission.

Referring again to FIG. 6, input cable 30 terminates at terminals 112 and 114. Similarly, output cable 32 terminates at terminal 108 and output cable 34 terminates at terminal 110.

Figure 7:
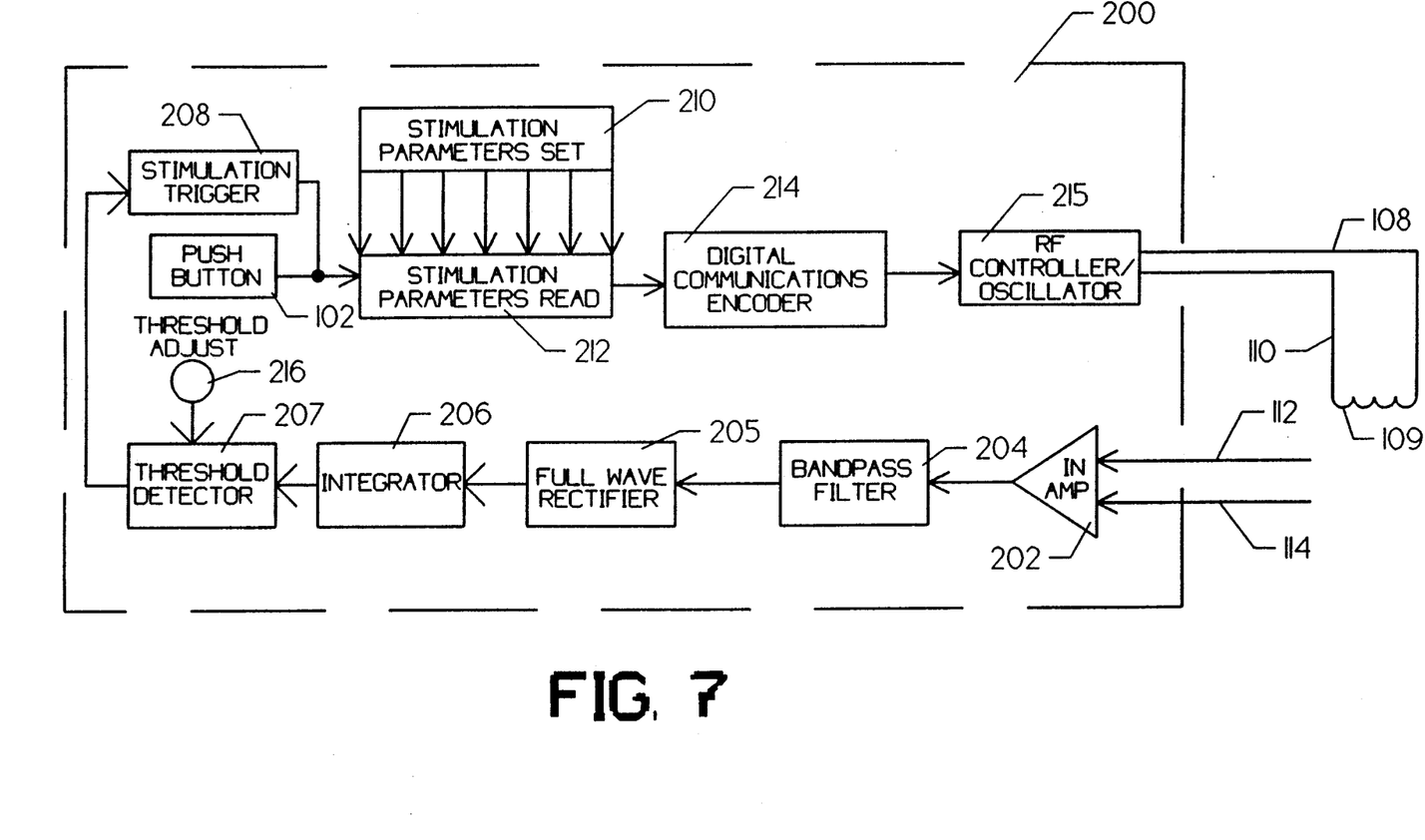
FIG. 7 is a block diagram of the electronic circuitry of the collar assembly.

FIG. 7 is a block diagram of electronic circuit 200. Each of the components of electronic circuit 200 is readily available in commercial form. Cable 30 from sensor 24, in this embodiment a microphone, (see also FIGS. 1 and 6), transfers the sensor signal via terminals 112 and 114 to In Amp 202, which provides initial amplification. Band pass filter 204 filters the amplified sensor signal to obtain the desired pass band. For sensor 24 as a breath or snoring activity sensor, for example, the desired pass band of band pass filter 204 corresponds to the frequency spectrum normally present in the snoring noise.

The filtered signal is presented to full wave rectifier 205 and then to integrator 206 which integrates the signal over the appropriate time. For sensor 24 as an audio sensor, one-tenth of a second is an appropriate integration time. The output of integrator 206 is a level representing the integrated sensor signal. This level is presented to threshold detector 207 having the threshold value set by threshold adjust 216. This ensures that whenever the integrated level exceeds the threshold set by threshold adjust 216, an enable signal is sent to stimulation trigger 208, for initiation of the stimulation pulse train.

As explained above, push button 102 is a single pole/single throw push button used to manually activate stimulation parameters read 212. This manual activation permits patient 100 to verify proper positioning of collar assembly 10 and mouthpiece 302.

Whether initiated automatically by stimulation trigger 208 or manually by push button 102, stimulation parameters read 212 initiates a stimulation pulse train based upon the parameters received from stimulation parameters set 210. These include without limitation:

A) CHANNEL NUMBER—The channel number of a particular remote electrode unit. If only two remote electrode units are used, they would be numbered 1 and 2. First, stimulation parameters would be set and/or programmed for channel 1 which might represent the left remote electrodes. Then the process would be repeated with independent stimulation parameter settings for remote electrode 2. If necessary, the design of the remote electrodes and the collar controller can be easily modified for any binary multiple of channels such as 2, 4, 8, etc. In the preferred embodiment the number is two.

B) ON-TIME—The duration of the stimulation period is typically 1–10 seconds.

C) RAMP-TIME—The time period during which the stimulation pulses ramp up in amplitude starting at the Threshold Amplitude and reach a maximum at the Operational Amplitude is typically 1–3 seconds (see below).

D) THRESHOLD AMPLITUDE—The amplitude at which a stimulation cycle begins is typically 5–20 volts.

E) OPERATIONAL AMPLITUDE—The maximum amplitude reached following a ramp up of amplitude is typically 10–40 volts.

F) PULSE REPETITION RATE—The rate at which the stimulation pulses are delivered during the On Time of stimulation is typically 30–90 pulses per second.

G) PULSE DURATION—The duration of time the stimulation amplitude is delivered each pulse is typically 50–300 microseconds.

H) POLARITY—The direction of current flow between the two electrodes of each remote electrode unit. Desired polarity depends upon muscle response.

Following the reading of the stimulation parameters by stimulation parameters read 212, the information is encoded as a digital bit stream by digital communications encoder 214, which is used by RF controller/oscillator 215 to deliver the digital bit stream data to antenna 109 via lines 108 and 110 in between continuous RF power transmissions.

Figure 8:
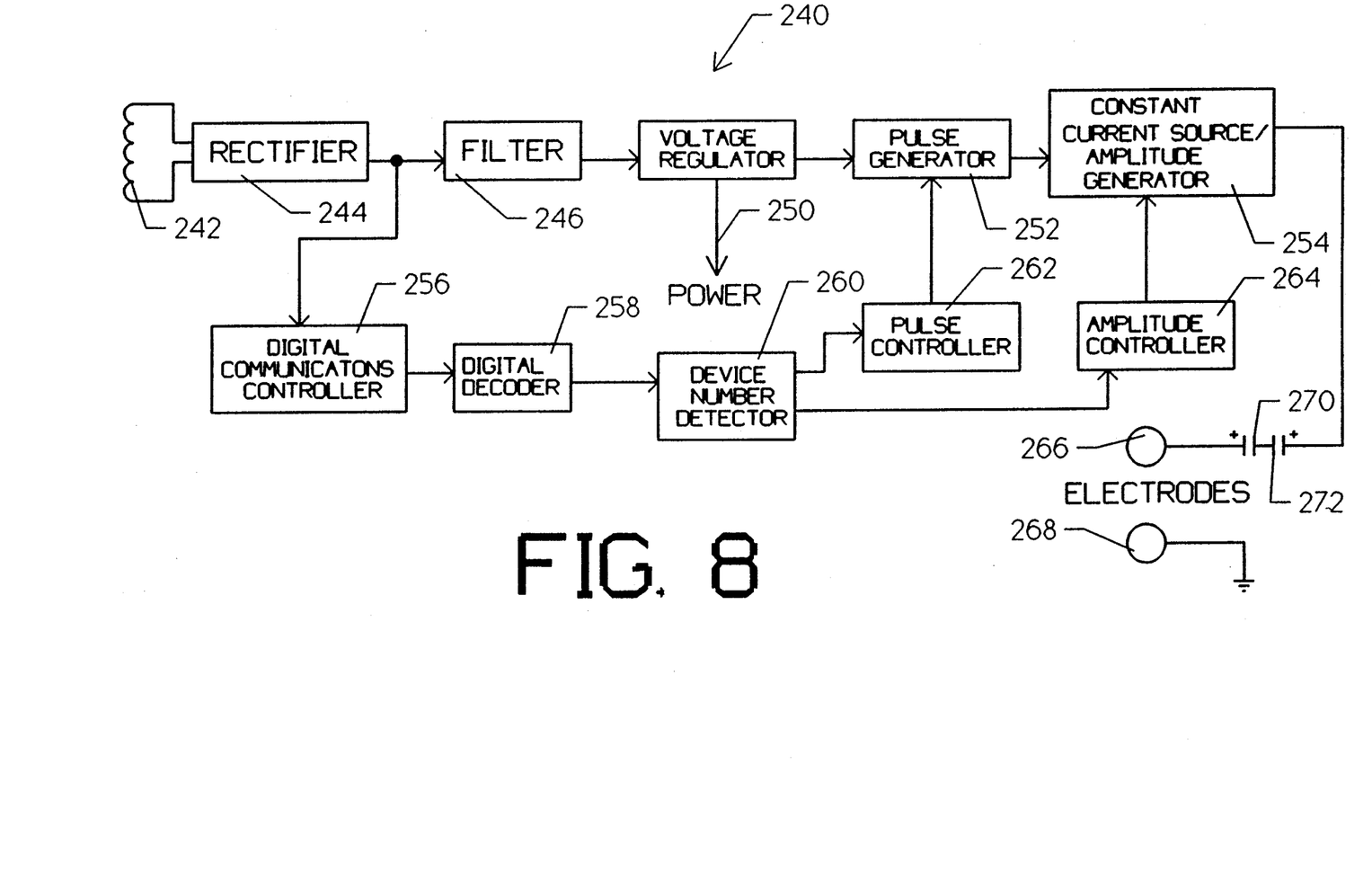
FIG. 8 is a block diagram of the electronic circuitry of the remote electrodes.

FIG. 8 is a block diagram 240 of the electrical circuitry associated with the remote electrodes. The continuous RF power transmission is received by the remote electrode unit antenna 242. This energy is rectified by rectifier 244 and filtered by filter 246. This energy stream is regulated by the voltage regulator having power output 250 which is used to supply power to the circuitry of the remote electrode unit. This regulated supply is independent of antenna coupling of collar antennae 26 and 28 and remote electrode unit antenna 242 within a certain range of coupling.

Digital communications detector 256 monitors the unfiltered rectified RF signal and synchronizes on the digital bit stream being transmitted. The bit stream is decoded by digital decoder 258 into the stimulation parameters A)–H) discussed above.

Device number detector 260 responds only if the correct device number is addressed. If this is the remote electrode being addressed, digital decoder 258 enables pulse controller 262 to trigger pulse generator 252 to generate a stimulation pulse stream in accordance with the received stimulation parameters. Constant current source/amplitude generator 254 delivers stimulation pulses to capacitors 270 and 272, which decouple any direct current components. The resulting signal is applied to electrodes 266 and 268 for stimulation of the musculature of the upper airway.

Figure 9:
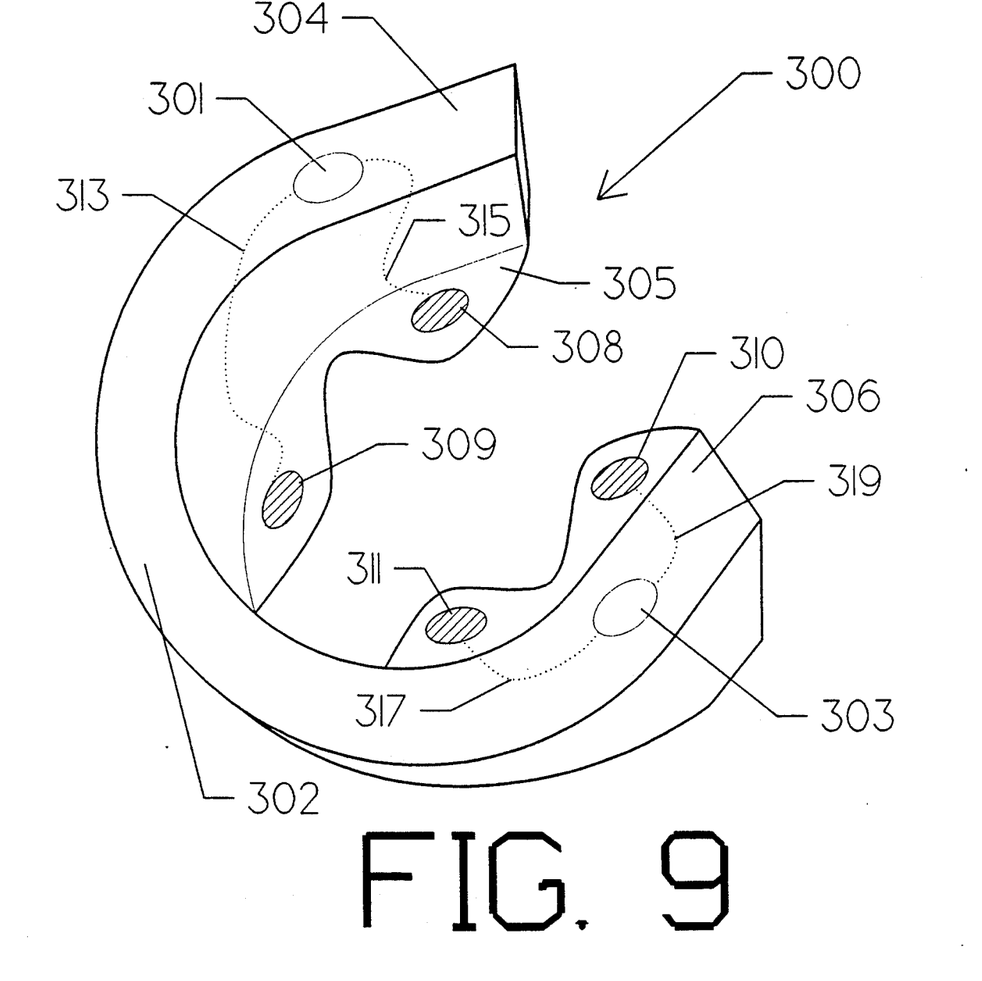
FIG. 9 is a perspective view of a mouthpiece having remote electrodes.

FIG. 9 is a perspective view 300 of mouthpiece 302. It is fabricated from a soft, comfortable, and safe plastic or rubber material suitable for intraoral use by patient 100. Mouthpiece 302 is preferably fitted to patient 100 to ensure mechanical stability during use. For most adults, the major size difference will reside in the lengths of ends 304 and 306 with the larger sizes for larger patients.

Fixedly attached to the lower interior walls of ends 304 and 306 is interior flap 305. This flap holds to electrodes which provide the stimulation signals to the tissue. Interior flap 305 is intentionally flexible to conform to the intraoral cavity of patient 100.

Fixedly attached to interior flap 305 are remote electrodes 308, 309, 310, and 311, respectively. Remote electrodes 308 and 309 are coupled to electronics module 301 (see also FIG. 7) via cables 315 and 313, respectively. Similarly, electronics mode 303 is coupled to remote electrodes 310 and 311 via cables 319 and 317, respectively. Electronic modules 301 and 303, along with cables 313, 315, 317, and 319 are imbedded within the material of mouth piece 302 to ensure that they are not disturbed during normal use.

Figure 10:
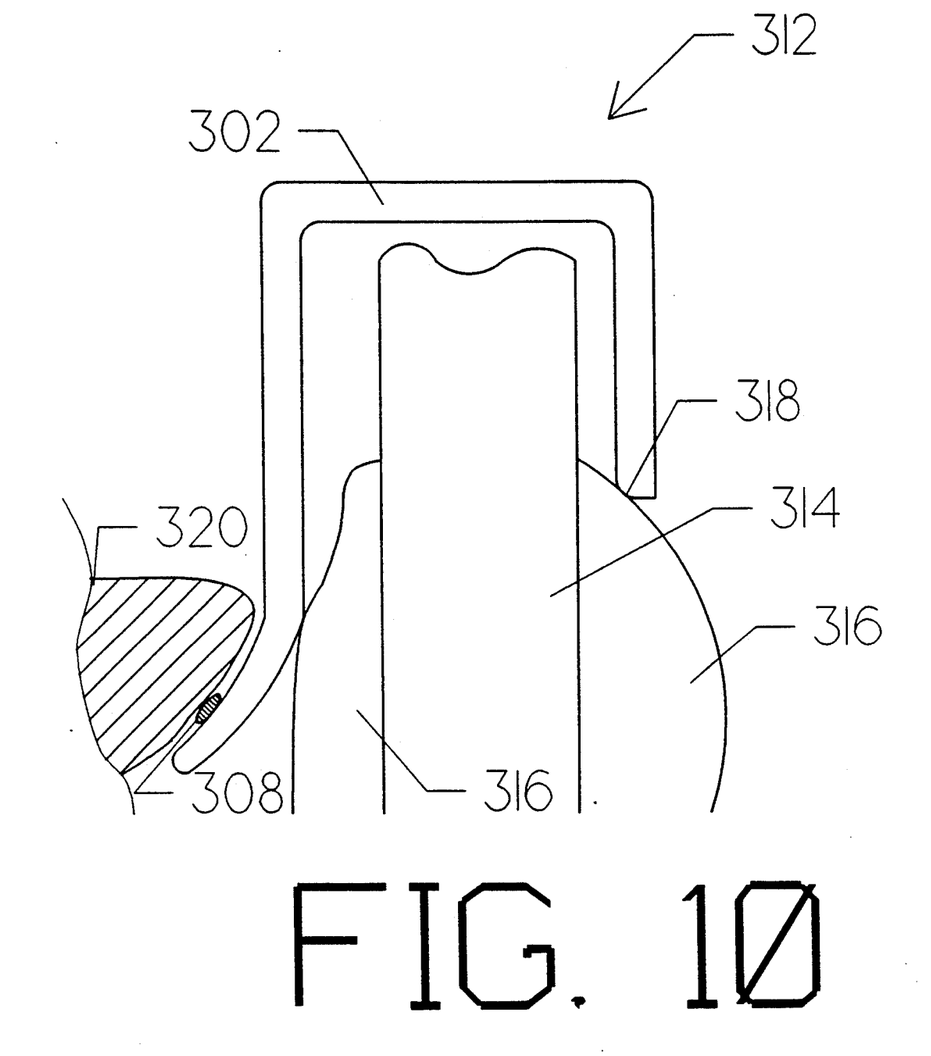
FIG. 10 is a closeup view showing the remote electrode/tissue contact maintained by the mouthpiece.

FIG. 10 is a closeup partially sectioned view 312 of mouthpiece 302. In proper operation, the section of mouthpiece 302 covers molar 314 as shown. This positions edge 318 firmly against the outer surface of gum tissue 316. The result is that interior flap 305 positions remote electrode 308 in firm contact with the base of tongue 320. Remote electrodes 309, 310, and 311 (not shown in this view) are similarly positioned.

Having thus described the pertinent details of the preferred embodiments, those of skill in the art will be readily able to employ the teachings found herein to practice yet other embodiments of the invention within the scope of the claims hereto attached.

What is claimed is:

1. An apparatus for treating obstruction of an upper air passageway of a patient comprising:
   a. means for sensing onset of an obstructive sleep apnea episode;
   b. means coupled to said sensing means for generating muscle stimulating signals;
   c. electrode means for transferring said muscle stimulating signals to muscle tissue of said upper air passageway of said patient;
   d. means coupled to said generating means and said electrode means for coupling said muscle stimulating signals from said generating means to said electrode means; and
   e. means attached to said sensing means, said generating means, and said coupling means for maintaining said sensing means, said generating means, and said coupling means in proximity to said patient.

2. An apparatus according to claim 1 wherein said coupling means comprises a radio frequency transmitter.

3. An apparatus according to claim 2 wherein said coupling means further comprises a radio frequency antenna coupled to said radio frequency transmitter.

4. An apparatus according to claim 3 wherein said maintaining means comprises a collar.

5. An apparatus according to claim 4 wherein said collar includes positioning means.

6. An apparatus according to claim 5 wherein said sensing means comprises an audio sensor.

7. An apparatus according to claim 5 wherein said sensing means comprises an activity sensor.

8. An apparatus according to claim 5 wherein said sensing means comprises an oximeter.

9. An apparatus according to claim 5 wherein said sensing means comprises an air flow meter.

10. A method of treating obstructive sleep apnea comprising:
    a. generating an electrical muscle stimulation signal;
    b. transmitting said electrical muscles stimulation signal using a radio frequency signal;
    c. receiving said radio frequency signal at a remote electrode means; and
    d. using said electrode means to transfer said muscle stimulating signals to muscle tissue of said upper air passageway of a patient.

11. A method according to claim 10 further comprising sensing onset of an apnea event.

12. A method according to claim 11 further comprising initiating said generating step in response to said sensing of said onset of said apnea event.

13. An apparatus for treating a patient comprising:
    a. means for generating muscle stimulating signals;
    b. electrode means for transferring said muscle stimulating signals to muscle tissue of said upper air passageway of said patient;
    c. means coupled to said generating means and said electrode means for coupling said muscle stimulating signals from said generating means to said electrode means; and
    d. means attached to said generating means and said coupling means for maintaining said generating means and said coupling means in proximity to said patient.

14. An apparatus according to claim 13 wherein said coupling means further comprises a radio frequency transmitter.

* * * * *